United States Patent [19]

Moore

[11] Patent Number: 4,466,439

[45] Date of Patent: Aug. 21, 1984

[54] DEVICE AND METHOD FOR INDUCING BRADYCARDIA

[76] Inventor: John H. Moore, 5389 Orchard Hill South, Kalamazoo, Mich. 49009

[21] Appl. No.: 346,497

[22] Filed: Feb. 8, 1982

[51] Int. Cl.³ .............................................. A61F 7/00
[52] U.S. Cl. .................................................. 128/402
[58] Field of Search ............... 128/399, 400, 401, 402, 128/419 PG

[56] References Cited

U.S. PATENT DOCUMENTS

| | | |
|---|---|---|
| 750,104 | 1/1904 | Eggers . |
| 1,004,192 | 9/1911 | Phelan . |
| 1,473,506 | 11/1923 | Nessler . |
| 1,627,523 | 5/1927 | Morris . |
| 1,739,625 | 12/1929 | Wolters . |
| 1,964,655 | 6/1934 | Williamson ........................ 128/258 |
| 2,562,121 | 7/1951 | Poux .................................... 150/2.2 |
| 2,726,658 | 12/1955 | Chessey ............................... 128/400 |
| 3,064,649 | 11/1962 | Fuson .................................. 128/214 |
| 3,140,716 | 7/1964 | Harrison et al. .................... 128/399 |
| 3,696,814 | 10/1972 | Umemoto ............................. 128/38 |
| 3,871,381 | 3/1975 | Roslonski ............................ 128/400 |
| 3,889,684 | 6/1975 | Lebold ................................. 128/402 |
| 3,897,790 | 8/1975 | Magilton et al. .................... 128/400 |
| 3,916,911 | 11/1975 | Sauder et al. ....................... 128/400 |
| 3,918,458 | 11/1975 | Nethery ............................... 128/400 |
| 4,108,146 | 8/1978 | Golden ................................ 128/400 |
| 4,112,943 | 9/1978 | Adams ................................ 128/24.1 |
| 4,118,946 | 10/1978 | Tubin ................................. 62/514 R |
| 4,149,529 | 4/1979 | Copeland et al. .................. 128/24.1 |
| 4,149,541 | 4/1979 | Gammons et al. .................. 128/400 |
| 4,154,245 | 5/1979 | Daily .................................... 128/400 |
| 4,177,816 | 12/1979 | Torgeson ............................. 128/400 |

OTHER PUBLICATIONS

*Gray's Anatomy,* Chapter 12, Parts VI, VII, and X, pp. 924–931 and 936–944.
J. Finley, J. Bonet & M. Waxman, *Autonomic Pathways Responsible for Bradycardia on Facial Immersion,* Journal of Applied Physiology, vol. 47(6), pp. 1218–1222, (Dec. 1979).
R. Strauss, *Diving Medicine,* pp. 259–261 and 279–282.
B. W. Shragge, S. B. Digermess, & E. H. Blackstone, *Complete Recovery of the Heart Following Exposure to Profound Hypothermia,* 81 Journal of Thoracic and Cardiovascular Surgery 455 (1981).
R. K. Khurana, S. Watabiki, J. R. Hebel, R. Toro, & E. Nelson, *Cold Face Test in the Assessment of Trigeminal--Brainstem-Vagal Function in Humans,* 7(2), Annals of Neurology 144 (1980).
N. B. Oldridge, G. J. F. Heigenhauser, J. R. Sutton, & N. L. Jones, *Resting and Exercise Heart Rate with Apnea and Facial Immersion in Female Swimmers,* 45(6) Journal of Applied Physiology 875 (1978).
J. LeBlanc, J. Cote, S. Dulac, & F. Dulong-Turcot, *Effects of Age, Sex, and Physical Fitness on Responses to Local Cooling,* 44(5) Journal of Applied Physiology 813 (1978).
A. D. Baddeley, W. C. Cuccao, G. H. Edstrom, G. Weltman, & M. A. Willis, *Cognitive Efficiency of Divers Working in Cold Water,* 17(5) Human Factors 446 (Oct. 1975).

*Primary Examiner*—Stephen C. Pellegrino
*Attorney, Agent, or Firm*—Price, Heneveld, Huizenga & Cooper

[57] ABSTRACT

The specification discloses a device for inducing dive reflex, and the associated bradycardia and vasoconstriction in the human through the application of cold stimulus to the facial nerve, which communicates with the parasympathetic nervous system. The device comprises a pair of opposed temperature-controllable, face-engaging members and a tension member interconnecting and biasing the face-engaging members toward one another to secure the face-engaging members on the face over a portion of the area in which the facial nerve surfaces. A method of inducing dive reflex using the device is also disclosed.

22 Claims, 4 Drawing Figures

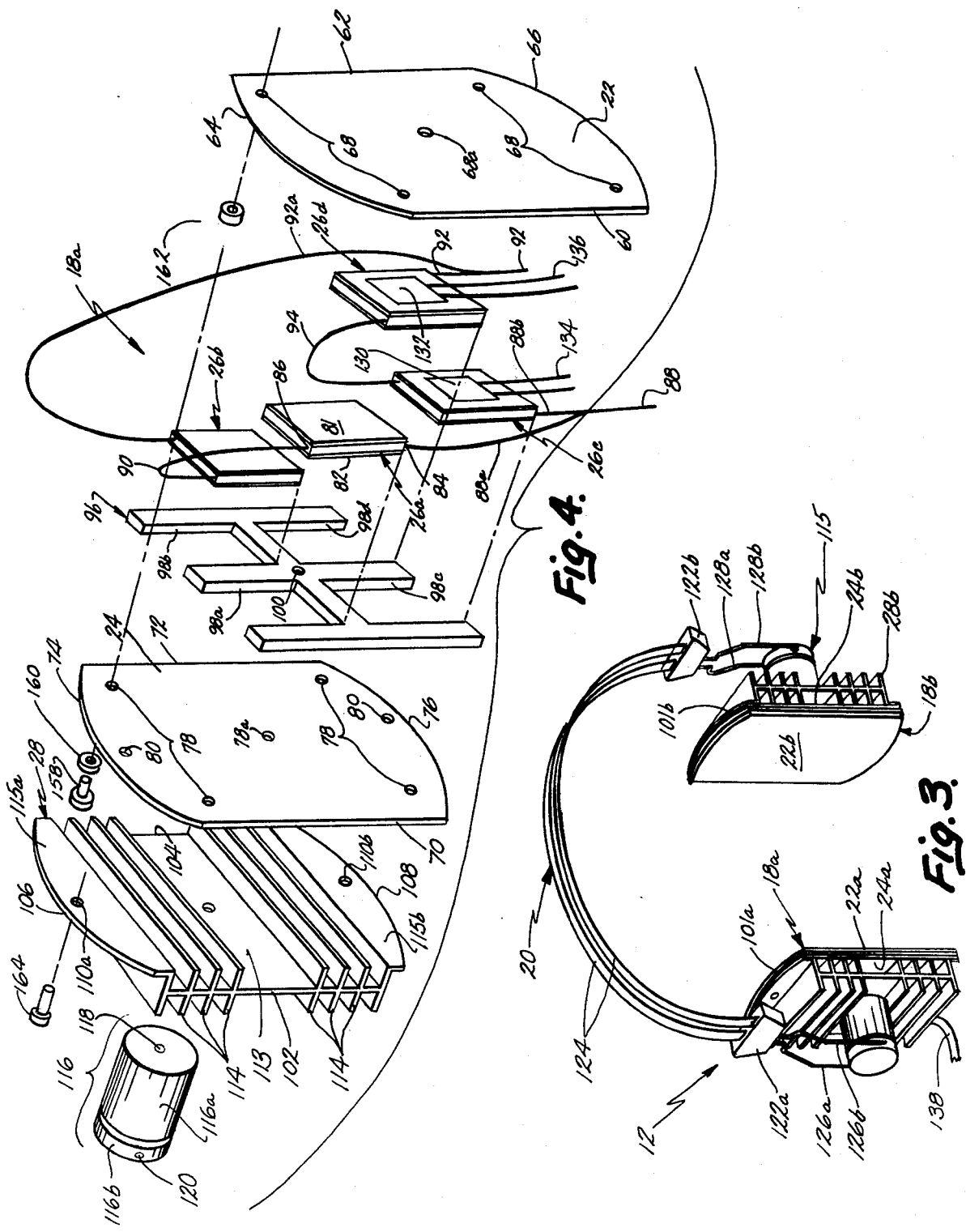

DEVICE AND METHOD FOR INDUCING BRADYCARDIA

BACKGROUND OF THE INVENTION

The present invention relates to medical devices and methods of using same, and more particularly such devices and methods for producing bradycardia in the human body.

Dive reflex, also known as diving reflex, is the mechanism through which the human body defends itself from hypothermia and resulting death, when submerged in cold water. The reflex is most graphically illustrated by the resuscitation of children, who have been submersed in farm ponds during the winter for periods exceeding the threeminute brain-death criterion. In dive reflex, the body, through selective vasoconstriction, isolates those tissues with extended anaerobic capability from those with relatively little anaerobic capability (the heart and brain). Consequently, circulation to the extremeties is greatly diminished, while circulation to the brain and heart continues at generally adequate levels. Additionally, the pulse-rate slows and a relatively constant blood pressure is maintained. Typically, the resulting minimum dive-reflex pulse-rate is approximately 60 to 70 percent of the quiescent rate. By trunking blood to the brain and heart, and slowing the pulse-rate, the body is able to supply the required oxygen to both the brain and the heart for extended periods of cold water submersion.

Although the dive reflex phenomenon has been known for a considerable period of time, the triggering mechanism has only recently been determined. Through selective anatomica immersion, it has been determined that the receptor mechanism is located in the face. See J. Finley et al, *Autonomic Pathways Responsible for Bradycardia on Facial Immersion,* Journal of Applied Physiology, Volume 47(6), Pages 1218-22 (December 1979). More recently, it has been hypothesized that the triggering receptor is the facial nerve which surfaces at the cheeks, forward of the ears to the nose. The facial nerve communicates with the auricular branch of the vagus nerve, which provides the autonomic pathway to the heart through the general visceral efferent fibers (parasympathetic branch of the vagus nerve). The application of a cold stimulus to the facial nerve induces dive reflex and slows the pulse-rate through its communication with the vagus nerve.

SUMMARY OF THE INVENTION

I have conceived that if dive reflex can be induced in a controlled environment, a considerable workload can be removed from the heart e.g., during post-infarction convalesscent periods. Such a pulse-rate reduction, undder constant blood pressure, would facilitate the recovery of patients due to the reduced requirement for oxygen by the heart. Additionally, because the blood supply to the extremeties is greatly reduced during dive reflex through vasoconstriction, artificial inducement of the phenomenon could also be used to reduce traumatic bleeding in the extremeties.

Recognizing the medical benefits to be gained through the inducement of dive reflex, I have conceived a device and method for inducing the reflex without immersing the face in cold water. The device includes cheek-engaging means, means for mounting the cheek-engaging means on a person's face, more particularly over a portion of the area where the facial nerve surfaces, and means for controlling the temperature of the cheek-engaging means in a range sufficiently low to induce dive reflex through the application of cold stimulus to the facial nerve. The method includes the steps of providing a device having temperature-controllable face-engaging means, mounting the device on the face of a person with the face-engaging means covering a portion of the area where the facial nerve surfaces, and controlling the temperature of the face-engaging means in a range sufficiently low to induce dive reflex.

The device and method of the present invention have several medical applications. First, the workload on the heart may be reduced by inducing dive reflex, and the associated bradycardia, in that patient. Such induced bradycardia is especially beneficial to post-infarction patients, and those who may be bradycardial drug resistant. Second, traumatic bleeding in the extremeties may be reduced by inducing dive reflex, due to the fact that the associated vasoconstriction reduces the volume of blood circulated through the limbs.

These and other objects, advantages, and features of the invention will be more readily understood and appreciated by reference to the written specification and appended drawings.

BRIEF DESCRIPTION OF THE DRAWINGS

FIG. 3 is a perspective view of the headset of the device with the fabric covers removed; and FIG. 4 is an exploded perspective view of a face-engaging assembly of the headset.

DESCRIPTION OF THE PREFERRED EMBODIMENT

Figure 1:
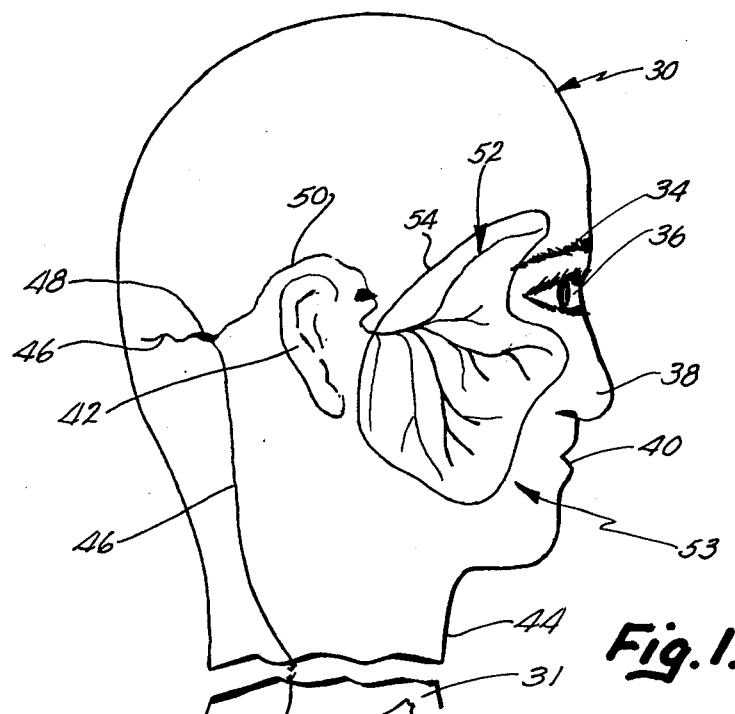
FIG. 1 is a fragmentary anatomical diagram showing the nerves of the parasympathetic nervous system pertinent to the present invention.

The portions of the parasympathetic nervous system pertinent to dive reflex are illustrated in FIG. 1. By way of orientation, head 30 includes eyebrow 34, eye 36, nose 38, mouth 40, and ear 42; and heart 32 is located in thoracic cavity 31. Vagus nerve 46 leads from the brain (not shown) through head 30 and neck 44 into thoracic cavity 31. Vagus nerve 46 incldues superior ganglion 48, located just rearward of ear 42, from which auricular nerve 50 branches. Facial nerve 52 leads from auricular nerve 50 opposite superior ganglion 48 and surfaces over an area 54 of the patient's cheek 53. Area 54 extends widthwise from just forward of ear 42 to eyebrow 34, eye 36, nose 38, and mouth 40 and heightwise between an area above eyebrow 34 and an area below mouth 40. General visceral efferent fibers 56 extend from vagus nerve 46 and surface in heart 32 to control the heart and its pulse-rate.

Facial nerve 52, auricular nerve 50, vagus nerve 46, and general visceral efferent fibers 56 serve as the autonomic pathway through which dive reflex is effected. When cold stimulus is applied to at least a portion of area 54 in which facial nerve 52 surfaces, the parasympathetic nervous system slows the heartbeat communicating with heart 32 through auricular nerve 50, vagus nerve 46, and general visceral efferent fibers 56. Maximum heartbeat reduction is estimated to be 40 percent. The parasympathetic nervous system also causes vasoconstriction and its associated reduction in circulation to those body extremeties with extended anaerobic capability. Accordingly, dive reflx can be selectively induced by applying a carefully controlled temperature source to area 54 of cheeks 53 in which facial nerve 52 surfaces.

A device 10 for inducing dive reflex in the human body is illustrated in the drawings and generally includes headset 12 (FIGS. 2 and 3), control box 14 (FIG. 2), and pulse monitor 16. Headset 12 in turn includes a pair of opposed face-engaging assemblies 18a and 18b (FIG. 3) and tension assembly 20 interconnecting the two face-engaging assemblies. Each face-engaging assembly 18 (FIG. 4) comprises face-engaging plate 22, backing plate 24, a plurality of thermo-electric chips 26 secured therebetween, and heat sink 28 secured to backing plate 24 opposite the thermo-electric chips.

Device 10 is used (FIG. 2) by positioning headset 12 on the patient's cheeks 53 with each face-engaging assembly 18 covering area 54 where facial nerve 52 surfaces (see also FIG. 1). Pulse monitor 16 is secured to the patient's chest 140. Thermo-electric chips 26 are then activated so that face plate 22 becomes cool and backing plate 24 becomes warm. As face-engaging plate 22 becomes cool, cold stimulus is applied to facial nerve 52, inducing dive reflx, with its associated bradycardia and vasoconstriction. Through control box 14, the temperature of face plates 22 may be regulated to a preselected temperature corresponding; to a predetermined percentage reduction in pulse-rate. Control unit 14 may alternatively maintain a predetermined pulse-rate as sensed by monitor 16, by regulating the temperature of face plates 22.

Face-engaging assemblies 18a and 18b (FIG. 3) are generally identical to one another. Accordingly, only assembly 18a (FIG. 4) will be described in detail. Face plate 22 is generally planar and is constructed of heavy-gauge aluminum or a semi-rigid, thermally-conductive polymer. Plate 22 is defined by two generally parallel side edges 60 and 62 and outwardly concave upper and lower edges 64 and 66. Five threaded apertures 68 extend through face plate 22. Backing plate 24 is similar to face plate 22, being also generally planar and constructed of heavy-gauge aluminum or a semi-rigid, thermally-conductive polymer. The silhouette of backing plate 24 which is defined by generally parallel side edges 70 and 72 and concave upper and lower edges 74 and 76 is identical to that of plate 22. Apertures 78 extend through backing plate 24 and are generally aligned with apertures 68 in plate 22 when the plates are aligned with one another. Additionally, two threaded apertures 80 extend through plate 24 proximate upper and lower edges 74 and 76.

Thermo-electric chips, or solid state heat pumps, 26 are generally well known to those having ordinary skill in the art. One thermo-electric chip particularly well suited to the present invention is that sold as model number CP 1.4-71-06L by Materials Electronic Products Corporation of Trenton, N.J. Each of chips 26 is generally identical to one another, and inclues a cold ceramic surface 81, hot ceramic surface 82, positive terminal 84, and negative terminal 86. When a voltage is applied across terminals 84 and 86, heat is transferred from cold surface 81 to hot surface 82 so that surface 81 becomes relatively cold and surface 82 becomes relatively hot. Chips 26a and 26b are connected in series through lines 88a, 90, and 92a. Similarly, chips 26c and 26d are connected in series by lines 88b, 94, and 92b. Chip pair 26a and 26b is connected in parallel with chip pair 26c and 26d to lines 88 and 92.

Insulation block 96 is also positioned between plates 22 and 24 and defines four generally identical pockets 98, each of which closely receives one of chips 26. Insulation 96 is a generally planar, rectangular piece, fabricated from a thermally and electrically non-conductive polymer or any other material having similar characteristics. Aperture 100 extends through a central portion of insulation 96. The thickness of insulation 96 is generally identical to the thickness of each of chips 26 and, in the preferred embodiment, is approximately 0.15 inches.

Face plate 22 and backing plate 24 are secured together entrapping and compressing insulation 96 and chips 26 therebetween, with each of chips 26 positioned within one of pockets 98. Screws such as 158 are inserted through each of apertures 68 and secured in one of apertures 78 to draw plates 22 and 24 together. Fiber washer 160 is positioned on screw 158 between screw head 158a and plate 24, and fiber washer 162 is positioned on screw 158 between plates 22 and 24 to insure that the screws do not conduct heat between the plates. The screw located in apertures 78a and 68a also passes through aperture 100 in insulation 96. Thermo-electric grease is applied to both the hot and cold faces of each of the chips 26 prior to mating with face plate 22 and backing plate 24, to facilitate heat transfer. When securely fastened, each of chips 26 is compressed between the plates, with plate 22 engaging each of front surfaces 81 and plate 24 engaging each of hot surfaces 82. After plates 22 and 24 are secured together, silicon 101 (see FIG. 3) is injected between the plates to provide additional insulation.

Heat sink 28 is fabricated from aluminum and connected to backing plate 24 opposite chips 26. Heat sink 28 includes generally parallel side walls 102 and 104 as well as concave upper and lower edges 106 and 108, all of which generally align with edges 70, 72, 74, and 76, respectively, on plate 24. The heat sink further comprises backbone plate 113 from which a plurality of transverse heat-dissipating fins 114 extend. Plate 113 defines central aperture 166. Securing flanges 115a and 115b are generally parallel to plate 113 and extend from outermost fins 114a and 114b, respectively. Apertures 110a and 110b extend through flanges 115a and 115b proximate upper and lower edges 106 and 108, respectively, and align with apertures 80 in backing plate 24. Thermo-electric grease, to facilitate heat transfer, is applied between heat sink 28 and backing plate 24. Heat sink 28 is secured to backing plate 24 by screws such as 164 extending through apertures 110 and secured in apertures 80. Each of fins 114 engages plate 24 to dissipate heat therefrom. Of course, other cooling means could be substituted for heat sink 28, for example liquid cooling.

A rubberized thermally-conductive fabric cover 168 (shown in phantom in FIG. 2) may optionally be installed over assembly 18, more particularly face plate 22 to improve the comfort of device 10.

Swivel mount 116 is well known and includes two generally cylindrical pieces 116a and 116b which pivot with respect to one another. Piece 116a defines a threaded bore 118 so that assembly 116 may be secured to heat sink 28 by inserting a screw through aperture 166 and into bore 118. Two recesses 120 (one not visible) are located in generally opposite sides of piece 116b.

Tension assembly 26 (FIG. 3) is also generally well known in the art, and in the preferred embodiment is identical to tension assembly found on stereo headphones. More particularly, tension assembly 20 includes two plastic brackets 122a and 122b, and two tension members 124 connected to and extending therebetween. Fingers 126a and 126b are frictionally slidably mounted in bracket 122a and extend into recesses 120 on swivel piece 116b (see FIG. 4) to secure tension bar 20 to face-engaging assembly 18a. Similarly, fingers 128a and 128b are slidably mounted in bracket 122b and are secured to swivel assembly 116.

Figure 2:
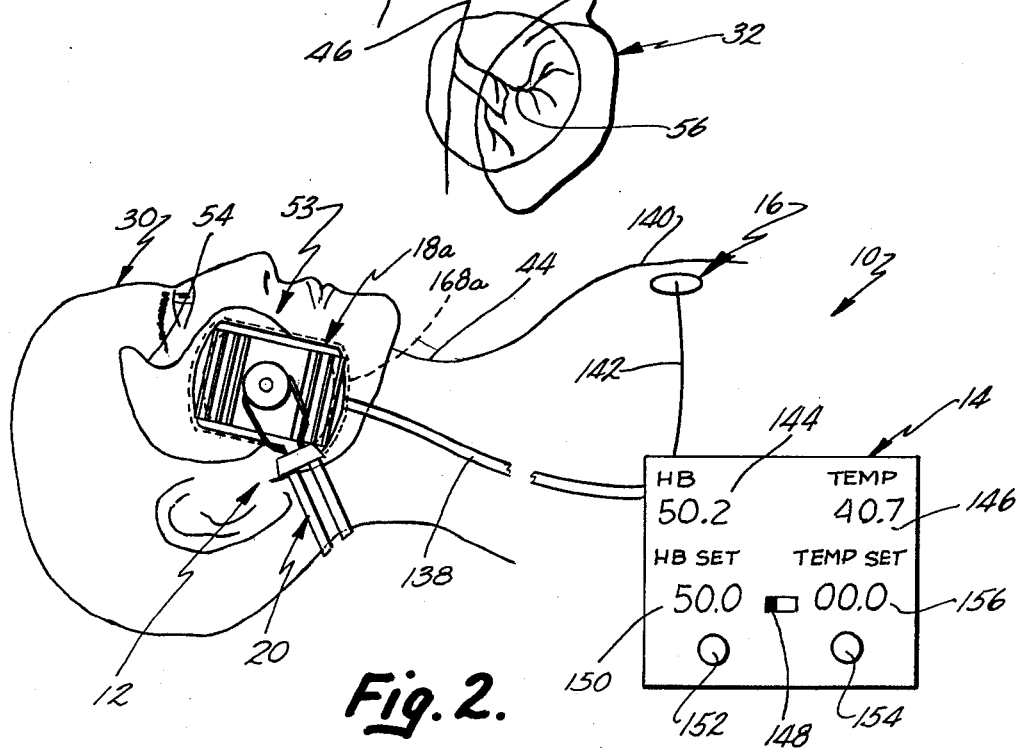
FIG. 2 is a fragmentary, elevational view of the device of the present invention mounted on a patient.

Thermocouples 130 and 132 are positioned between chips 26c and 26d, respectively, and face plate 22. These thermocouples are well known and sense the temperature of cold surfaces 81 of the thermo-electric chips. Lines 134 and 136 lead from thermocouples 130 and 132, respectively, and together with lines 88 and 92 comprise cable 138 (FIGS. 2 and 3) which leads to control unit 14 (FIG. 2). Pulse monitor 16 is also well known and is secured to chest 140. Line 142 interconnects monitor 16 with control unit 14.

Control unit 14 (FIG. 2) includes pulse-rate display 144 which displays the current pulse-rate sensed through monitor 16, and temperature display 146 which displays the current temperature sense at thermocouple 130 (see FIG. 4). Unit 14 further includes adjusting knobs 152 and 154 as well as pulse-rate-set display 150 and temperature set display 156 responsive respectively thereto. The temperature of face plates 22 may be controlled in either of two manners, as selected by switch 148 in control unit 14. When the switch is in its first position (as shown in FIG. 2), the desired pulse-rate may be selected on display 150 by turning adjusting knob 152 until the selected pulse-rate appears on the display. Control unit 14 will then, through control circuitry well known, regulate the current supplied to chips 26 to regulate the temperature of face plates 22 so that the desired pulse-rate is maintained as sensed by monitor 16. Suitable control circuitry is sold under model number 149 by Omega Engineering, Inc., of Stamford, Conn. When switch 148 is in a second opposite position, the desired temperature of plates 22 may be set by adjusting knob 154 until the desired temperature appears on display 156. Control unit 14 will then regulate current supplied to chips 26 to maintain plate 22 at the selected temperature. When switch 148 is in its first position, display 156 shows all zeroes to indicate that the temperature may not be set. Likewise, when switch 148 is in its second position, display 150 shows all zeroes to indicate that the pulse-rate may not be set.

Thermocouple 136 is connected to control circuitry within control unit 14 to deactivate device 10 and sound an audible warning if the temperature at the thermocouple exceeds a predetermined maximum parameter or falls below a minimum parameter to prevent scalding and freezing of the facial tissue. Such control circuitry is sold under model number 166 by Omega Engineering, Inc. Control circuitry is also included in control unit 14 to deactivate device 10 and sound an audible alarm if the pulse-rate, as sensed by monitor 16, exceeds a predetermined maximum rate or falls below a minimum rate.

OPERATION

Device 10 is used by first mounting headset 12 and pulse monitor 16 on the patient's body (FIG. 2). Each of face-engaging assemblies 18a, and more particularly face plates 22 are mounted to overlie a substantial portion of area 54 where facial nerve 52 surfaces. Tension bar 20 urges assemblies 18a and 18b toward one another to engage the patient's cheeks, or face, to secure headset 12 on the patient's head 30. Pulse monitor 16 is then secured to chest 140 in a well-known manner. Headset 12 and pulse monitor 16 are then connected to control unit 14 through cable 138 and line 142, respectively.

The temperature of plates 22 is then maintained, controlled, or regulated in a range sufficiently low to induce dive reflex, and the associated bradycardia and vasoconstriction, through facial nerve 52. It has been discovered that temperatures between 40° to 59° F. produce the most effective dive reflex with the pulse-rate being generally linear between these two temperatures. As cold stimulus is applied to facial nerve 52, the parasympathetic nervous system induces dive reflex in the patient, and more particularly induces bradycardia through facial nerve 52, auricular nerve 50, and vagus nerve 46. When face plates are maintained at a temperature of approximately 40° F., maximum bradycardia is effected and the pulse-rate is approximately 60 percent of its normal quiescent value.

The degree of bradycardia may be controlled in one of two manners, depending upon the position of switch 148 on control unit 14. First, the pulse-rate may be maintained at a preselected level; and second, the temperature of face plates 22 may be maintained at a preselected temperature. When switch 148 is in its first position as shown in FIG. 2, the desired pulse-rate may be set by adjusting knob 152 to display the desired value at display 150. Control unit 14 will then regulate the temperature of face plates 22 upwardly or downwardly to maintain the pulse-rate at this desired value. Control unit 14 will lower the temperature of plates 22 if the pulse-rate exceeds the preselected value and will raise the temperature of plates 22 if the pulse-rate falls below the preselected value to maintain the pulse-rate at or near the preselected value. Alternatively, when switch 148 is in a second, opposite position, the temperature of face plates 22 may be adjusted using knob 154 to display the desired temperature on display 156. The face plates will then be maintained at this value regardless of the current pulse-rate. In either control method, the current pulse-rate is displayed on display 144 and the current temperature of plate 22 is displayed at display 146.

In the event of a system malfunction, causing the temperature of face plate 22 to exceed a predetermined maximum parameter of fall below a predetermined minimum parameter, thermcouple 132 signals control unit 14 that the temperature of the face plates is outside of the acceptable temperature range. If the patient's pulse-rate exceeds the predetermined maximum rate or falls below the minimum rate, monitor 16 signals control unit 14 that the pulse rate is outside of the acceptable pulse-rate range. In either event, control unit 14 then cuts power to chips 26 and sounds an alarm indicating a system malfunction.

It should be understood that the above description is intended to be that of a preferred embodiment of the invention. Various changes and alterations might be made without departing from the spirit and broader aspects of the invention as set forth in the appended claims, which are to be interpreted in accordance with the principles of patent law, including the doctrine of equivalents.

The embodiments of the invention in which an exclusive property or privilege is claimed are defined as follows:

1. A device for inducing dive reflex in a person for medical treatment purposes comprising:
   cheek-engaging means;
   means for mounting said cheek-engaging means against a portion of at least one of the cheeks of said person, said cheek portion including an area where a portion of the facial nerve surfaces; and
   means for controlling the temperature of said cheek-engaging means in a range sufficiently low to induce dive reflex by the application of cold stimulus to said facial nerve, said temperature-controlling means including means for monitoring the pulse-rate of said person, said temperature-controlling means further including means responsive to said pulse-rate means for lowering the temperature of said cheek-engaging means when said pulse-rate exceeds a preselected value and for raising the temperature of said cheek-engaging means when said pulse-rate falls below said preselected value to maintain said pulse-rate at or near said preselected value.

2. A device as defined in claim 1 wherein said temperature-controlling means further comprises limit means for preventing the temperature of said cheek-engaging means from exceeding a maximum temperature and from falling below a minimum temperature to prevent scalding and freezing of the facial tissue.

3. A device as defined in claim 1 wherein said temperature-controlling means further comprises alarm means for sounding an audible alarm whenever said pulse-rate exceeds a predetermined maximum rate or falls below a minimum rate.

4. A device for inducing dive reflex in a person for medical treatment purposes comprising:
   cheek-engaging means;
   means for mounting said cheek-engaging means against a portion of at least one of the cheeks of said person, said cheek portion including an area where a portion of the facial nerve surfaces; and
   means for controlling the temperature of said cheek-engaging means in a range sufficiently low to induce dive reflex by the application of cold stimulus to said facial nerve, said temperature-controlling means including heat pump means for removing heat from said cheek-engaging means, said temperature-controlling means further including heat sink means operably connected to said heat pump means for dissipating said heat to said ambient air.

5. A device as defined in claim 4 wherein said heat pump means comprises a solid state heat pump.

6. A device as defined in claim 5 wherein said solid state heat pump comprises a thermo-electric chip.

7. A device for inducing dive reflex in a person for medical treatment purposes to reduce said person's pulse-rate or to reduce the circulation to said person's extremeties, said device comprising:
   a pair of opposed cheek-engaging members;
   means for securing said cheek-engaging members on the cheeks of said person over a portion of the region where the facial nerve, which communicates with the parasympathetic nervous system, surfaces; and
   means for controlling the temperature of said members in a range sufficiently low to induce dive reflex by the application of cold stimulus to said facial nerve, said temperature-controlling means including means for monitoring the pulse-rate of said person, said temperature-controlling means further including means responsive to said pulse-rate monitoring means for lowering the temperature of said cheek-engaging members when said pulse-rate exceeds a preselected value and for raising the temperature of said cheek-engaging members when said pulse-rate falls below said preselected value to maintain said heartbeat at or near said preselected value.

8. A device as defined in claim 7 wherein said temperature-controlling means further comprises limit means for preventing the temperature of said cheek-engaging members from exceeding a maximum temperature and from falling below a minimum temperature to prevent scalding and freezing of the facial tissue.

9. A device as defined in claim 7 wherein said temperature-controlling means further comprises alarm means for sounding an audible alarm whenever said pulse-rate exceeds a predetermined maximum rate or falls below a minimum rate.

10. A method for inducing dive reflex to slow the pulse-rate of a person for medical treatment purposes comprising the steps of:
    providing a device having temperature-controllable, face-engaging means;
    mounting said device on said person with said face-engaging means in engagement with a portion of the face of said person, said face portion including a portion of the area in which the facial nerve, which communicates with the parasympathetic nervous system, surfaces; and
    controlling the temperature of said face-engaging means within a range sufficiently low to induce dive reflex in said person.

11. A method as defined in claim 10 further comprising the step of monitoring the pulse-rate of said person, and wherein said controlling step comprises the steps of:
    raising said temperature when said pulse-rate falls below a preselected value; and
    lowering said temperature when said pulse-rate exceeds said preselected value, whereby said pulse-rate is maintained at or near said preselected value.

12. A method as defined in claim 11 further comprising:
    preventing said temperature from exceeding a maximum temperature to prevent scalding the facial tissue; and
    preventing said temperature from falling below a minimum temperature to prevent freezing said facial tissue.

13. A method as defined in claim 11 further comprising sounding an audible alarm whenever said pulse-rate exceeds a predetermined maximum rate or falls below a minimum rate.

14. A method as defined in claim 10 wherein said mounting step comprises biasing said face-engaging means against said portion of said face.

15. A method as defined in claim 10 further comprising providing a rubberized, fabric cover on said thermally conductive, face-engaging means to improve the comfort of said device.

16. A method as defined in claim 10 wherein said controlling step comprises controlling said temperature within a range of approximately 40° to 59° F.

17. A method of slowing the pulse-rate of a person for medical treatment purposes comprising the steps of:
    providing a device having temperature-controllable, cheek-engaging members;

mounting said device on said person with said members engaging a portion of the cheeks of said person, said cheek portion including a portion of the area in which the facial nerve, which communicates with the parasympathetic nervous system, surfaces; and controlling the temperature of said members in a range sufficiently low to induce bradycardia through said parasympathetic nervous system.

18. A method as defined in claim 17 further comprising the step of monitoring the pulse-rate of said person, and wherein said controlling step comprises the steps of:

raising said temperature when said pulse-rate falls below a preselected value; and lowering said temperature when said pulse-rate exceeds said preselected value, whereby said pulse-rate is maintained at or near said preselected value.

19. A method as defined in claim 18 further comprising:

preventing said temperature from exceeding a maximum temperature to prevent scalding the facial tissue; and preventing said temperature from falling below a minimum temperature to prevent freezing said facial tissue.

20. A method as defined in claim 18 further comprising sounding an audible alarm whenever said pulse-rate exceeds a predetermined maximum rate or falls below a minimum rate.

21. A method as defined in claim 17 wherein said mounting step comprises biasing said cheek-engaging members against said portion of said face.

22. A method as defined in claim 17 further comprising providing a rubberized, thermally conductive fabric cover on said cheek-engaging members to improve the comfort of said device.

* * * * *